United States Patent [19]

Villen Pascual

[11] Patent Number: 5,049,133
[45] Date of Patent: Sep. 17, 1991

[54] SINGLE-USE SAFETY SYRINGE

[76] Inventor: Joeé A. Villen Pascual, Compromiso de Caspe, 1, Valencia, Spain

[21] Appl. No.: 468,735

[22] Filed: Jan. 23, 1990

[30] Foreign Application Priority Data

Jan. 24, 1989 [ES] Spain ................................ 8900234

[51] Int. Cl.⁵ .............................................. A61M 5/00
[52] U.S. Cl. .................................. 604/110; 604/198; 604/240
[58] Field of Search ........ 604/110, 192, 194, 195-198, 604/240

[56] References Cited

U.S. PATENT DOCUMENTS

| | | | |
|---|---|---|---|
| 3,848,579 | 11/1974 | Villa-Real | 178/276 |
| 4,687,467 | 8/1987 | Cygielski | 604/110 |
| 4,781,684 | 11/1988 | Trenner | 604/110 |
| 4,838,863 | 6/1989 | Allard et al. | 604/195 |
| 4,838,869 | 6/1989 | Allard | 604/195 |
| 4,874,832 | 10/1989 | Lindemann et al. | 404/195 |
| 4,955,870 | 9/1990 | Ridderheime et al. | 604/195 |

FOREIGN PATENT DOCUMENTS

| | | | |
|---|---|---|---|
| WO89/00435 | 1/1989 | PCT Int'l Appl. | 604/110 |
| 2210270 | 6/1989 | United Kingdom | 604/110 |

Primary Examiner—Stephen C. Pellegrino
Assistant Examiner—Michael Rafa
Attorney, Agent, or Firm—Darby & Darby

[57] ABSTRACT

The present invention relates to a safety-syringe providing a needle with a hollow core having a spring coiled around the needle. The spring is capable of expanding to retract the needle into the body of the syringe. A pressure hinge is provided with a plurality of teeth-shaped triggers for retaining the needle in a position for use and for preventing the piston from moving after use. Further, a vacuum may be provided within the piston for facilitating in the retraction of the needle into the syringe.

6 Claims, 1 Drawing Sheet

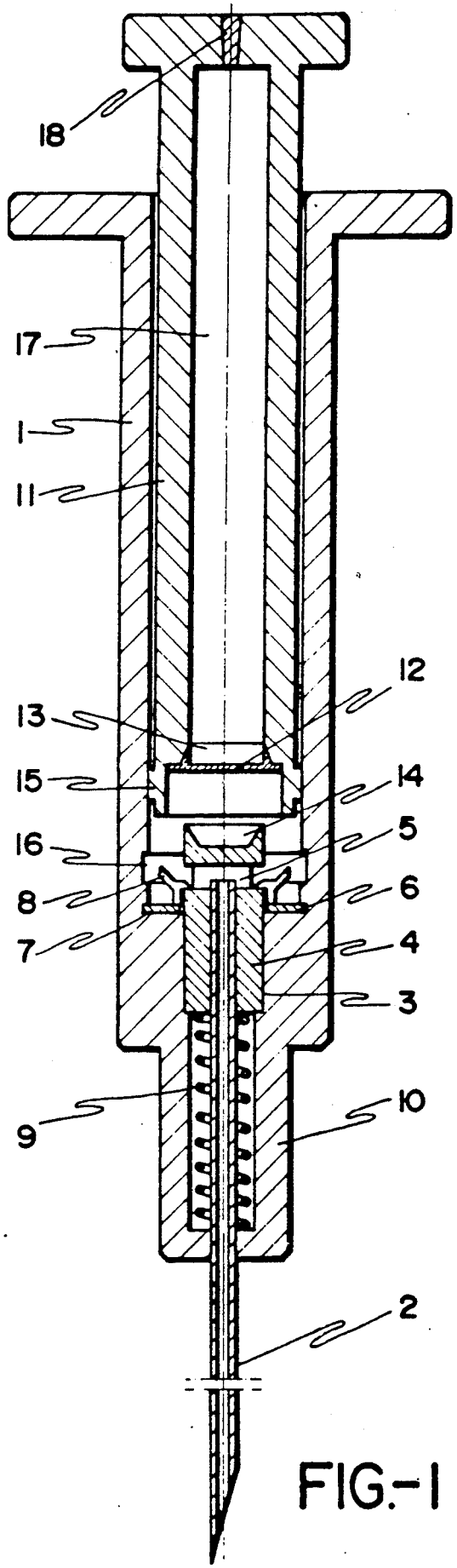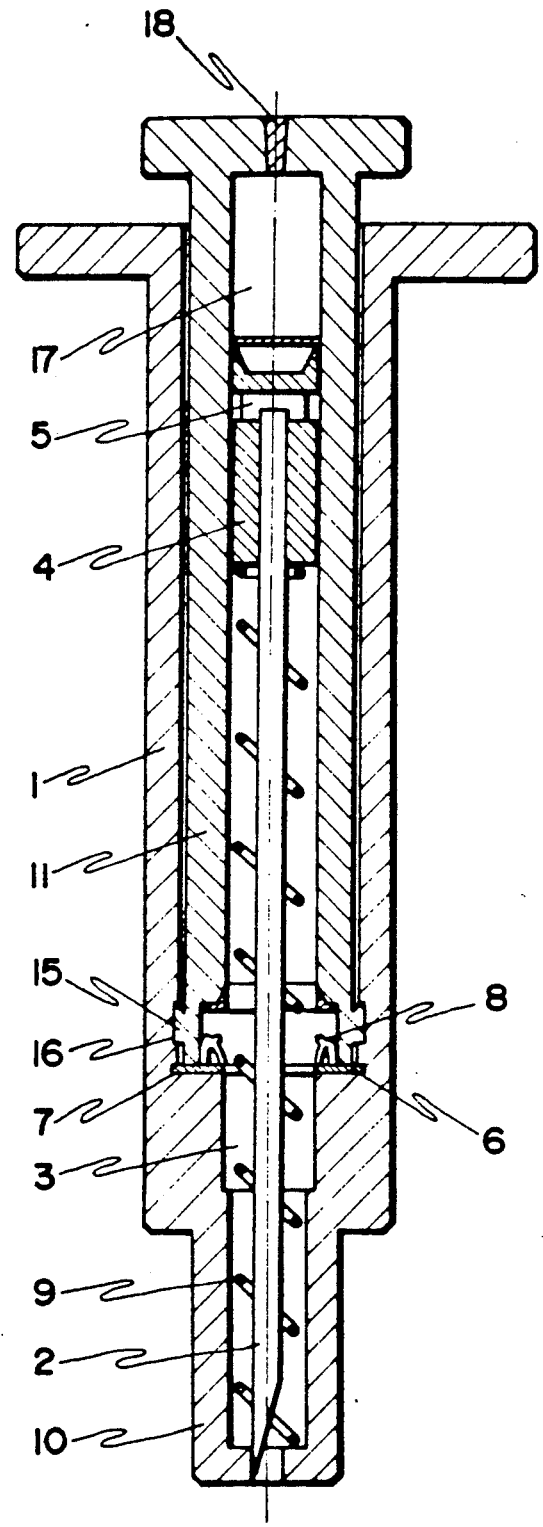

SINGLE-USE SAFETY SYRINGE

Once used, this syringe is rendered unsuable automatically, thereby making it impossible for further use.

The syringe is made of a cylindrical receptor for the product to be injected and a propelling piston. The injectable needle features a head which is housed into a extension of the body of the syringe, thus becoming secured by a device conformed by several triggers which become unhooked when the piston reaches its maximum run.

The head of the needle features a cutting device which punches the membrane closing the piston's hollow chamber, where a vacuum was created previously, such that once the membrane is punctured the needle is absorbed into the piston's hollow core assisted by an expansion spring leaning against the head. With the needle inside the piston, the syringe can not be reused.

When the piston reaches it longest run, it becomes engaged and can not be recuperated.

DESCRIPTION OF INVENTION

The object of the invention is a single-use safety syringe, namely a syringe that is rendered useless after a single use, such that it may not be reused. This is achieved by retracting the needle into the piston's hollow core.

The purpose of the invention is to make a contribution toward an improved and safer use of injectable medication, thus reducing accidents and contagion derived from improper handling.

The syringe is made of the following components:
a) Outer body, which in turn is composed of:
   Retaining chamber of the propeller spring.
   Expansion (not essential) for the needle.
   Expansion to engage the retention hinge.
   Second expansion (dentate) to retain and block the piston.
b) Piston, made of the following parts:
   Main body (hollow cylinder) with a proximal circular expansion fitted with a dentate border for blocking. Inner lumen equal to the outer diameter of the head of the needle.
   Distal membrane, forming the proximal wall of the piston, for appropriate push of injectable fluids, and contributing to the formation of a vacuum within the piston.
   Vacuum hole, permits forming a vacuum.
c) Needle, made of the following parts:
   Puncture tube (according to standard calipers).
   Sliding puncturing body. It's function is to punch the membrane. It may be propelled by the spring to slide within the piston's hollow core and/or become aspirated by the vacuum effect within the piston.
   Likewise, it also features a narrow passage which allows fluid displacement into the needle, and retains the body of the needle though the teeth of the retention hinge.
d) Retention hinge: its object is to retain the needle body when it is mounted, likewise it also blocks the body until the piston wall releases the body c), by pressing the outermost ends of the three teeth.

This device has the shape of a crown, with three retention teeth or triggers come off its central core, continuing on in a "V" arrangement with such an inclination that their retraction is possible.

e) Propeller spring: When the spring is released it is slightly longer than the portion of the needle that is lodged outside the sliding body of the needle, thus ensuring its lodging into the watertight compartment within the device.
f) Membrane: Its function was referred to in section b). It is worth noting its low degree of porosity and hardness, as well as its scarce thickness and high fragility in order not to be extremely resistant to punching.

DESCRIPTION OF DRAWINGS

In order to improve understanding of the invention, a set of two drawings representing the single-use safety syringe in two different positions is enclosed along with this memorial:

FIG. 1: Represents a longitudinal section of the syringe with all its components arranged for use as if it were a normal hypodermic syringe.

FIG. 2: Represents the hypodermic syringe showing the needle already retracted.

DETAILED DESCRIPTION

As can be seen from the drawings, the hypodermic syringe presents at one end of its body (1), an expansion for the needle (2), the lodging (3) where the head of the needle (4) is secured, which is fitted with lateral passages (5) allowing for medication flow into the needle's inner core (2). The head of the needle (4) is secured into ready-for-use position by a pressure hinge (6) retained in place by an expansion (7) of the body, whose hinge is provided by three or more teeth (8) arranged as triggers, thus retaining the head of the needle against the opposite effect of the expansion spring (9) coiled around an extension (10) of the body, between the bottom of the extension and the head (4) of the needle (2).

The piston (11) is made of a hollow body with its lower end sealed by a membrane (12) and by a cylindrical wall (13) used for pushing against the retention teeth of the head (4) and of the needle (2) at the end of the run of the piston (11).

The head (4) of the needle (2) conforms a cutting crown (14) which faces the membrane (12) of the piston.

The cylindrical expansion of the piston (11) presents a peripheral relief (15) on the area of contact of the walls of the body which is to fit into the corresponding notch (16) located near the triggers (8) of the needle (2).

The lumen (17) of the piston (11) presents a diameter similar to that of the head (4) of the needle (2), in order to allow for its lodging when propelled by the spring (9).

The vacuum is produced in the lumen (17) of the piston (11), which is closed by an airtight cap (18) facilitating penetration of the head (4) of the needle (2) when it is released, the push of the spring helps in this retraction.

I claim:
1. A single-use safety syringe comprising:
   a body for containing a fluid, said body having a projection and a chamber;
   a needle having a head end and a hollow core for receiving the fluid, said head end being positioned in said chamber below said projection when the syringe is in use;
   piston means positioned in said body above said needle for pushing the fluid into said needle when the syringe is in use;

a spring coiled around said needle below said head end and positioned in contact with said head end and said body, said spring expanding after use of the syringe so that said needle is propelled into the upper end of said body above said projection; and a pressure hinge positioned on said projection having a plurality of teeth-shaped triggers, said piston means having at its lower end retention means engaging the inner wall of said chamber in the vicinity of said triggers, whereby said triggers both retain said head end below said projection to prevent expansion of said spring as the syringe is in use and bear against said retention means to prevent motion of said piston means after deformation of said triggers by said piston means and expansion of said spring.

2. A single-use safety syringe according to claim 1, wherein said piston means comprises a piston having a hollow core and an upper and lower end, said lower end being sealed by a membrane, said piston having a cylindrical wall around said membrane which wall pushes against said triggers to cause the deformation of said triggers after use of the syringe.

3. A single-use safety syringe according to claim 2, wherein said head end of the needle has a cutting crown which faces said membrane of said piston for piercing the membrane.

4. A single-use safety syringe according to claim 1, wherein the inner wall of said chamber has notches therein in the vicinity of said triggers and said retention means comprises peripheral relief member on said piston means which engage said notches.

5. A single-use safety syringe according to claim 2, wherein said hollow core has a diameter which is approximately equal to the diameter of said head of the needle so that said needle is received in said hollow core after said spring has expanded.

6. A single-use safety syringe according to claim 3, wherein said hollow core has a vacuum, so that when said cutting crown pierces said membrane said vacuum serves to facilitate the retraction of said needle into said hollow core.

* * * * *

UNITED STATES PATENT AND TRADEMARK OFFICE
CERTIFICATE OF CORRECTION

PATENT NO. : 5,049,133

DATED : September 17, 1991

INVENTOR(S) : Jose Antonio Villan Pascual

It is certified that error appears in the above-identified patent and that said Letters Patent is hereby corrected as shown below:

Title page, item [76] Inventor: Jose A. Villan Pascual,
Compromiso de Caspe, 1-13ª
46007 Valencia, Spain Signed and Sealed this Twentieth Day of April, 1993

Attest:

MICHAEL K. KIRK

*Attesting Officer*  *Acting Commissioner of Patents and Trademarks*